(12) United States Patent
Sedic

(10) Patent No.: US 10,893,975 B2
(45) Date of Patent: Jan. 19, 2021

(54) MENSTRUAL CUPS AND METHODS OF USE

(71) Applicant: Filip Sedic, Shanghai (CN)

(72) Inventor: Filip Sedic, Shanghai (CN)

( * ) Notice: Subject to any disclaimer, the term of this patent is extended or adjusted under 35 U.S.C. 154(b) by 0 days.

(21) Appl. No.: 16/353,116

(22) Filed: Mar. 14, 2019

(65) Prior Publication Data

US 2019/0201231 A1     Jul. 4, 2019

Related U.S. Application Data

(63) Continuation of application No. 16/214,452, filed on Dec. 10, 2018.

(60) Provisional application No. 62/609,513, filed on Dec. 22, 2017.

(51) Int. Cl.
    *A61F 5/455*     (2006.01)
    *A61F 6/06*     (2006.01)

(52) U.S. Cl.
    CPC ............ *A61F 5/4553* (2013.01); *A61F 6/065* (2013.01)

(58) Field of Classification Search
    CPC ..... A61F 5/4552; A61F 13/2045; A61F 6/065
    See application file for complete search history.

(56) References Cited

U.S. PATENT DOCUMENTS

| | | | |
|---|---|---|---|
| 2,534,900 A | 1/1950 | Chalmers | |
| 3,404,682 A | 10/1968 | Waldron | |
| 3,626,942 A | 12/1971 | Waldron | |
| 3,845,766 A | 11/1974 | Zoller | |
| 4,681,572 A | 7/1987 | Tokarz et al. | |
| 5,295,984 A * | 3/1994 | Contente | A61K 9/0036 604/317 |
| 5,771,900 A | 6/1998 | Austin et al. | |
| 5,827,248 A | 10/1998 | Crawford | |
| 6,264,638 B1 * | 7/2001 | Contente | A61F 5/4553 604/285 |
| 6,540,728 B2 | 4/2003 | Zadini et al. | |
| 6,796,973 B1 | 9/2004 | Contente et al. | |
| 6,964,643 B2 | 11/2005 | Hovland et al. | |
| D746,452 S | 12/2015 | Petrova | |
| D760,897 S | 7/2016 | Teo | |
| 9,456,922 B2 | 10/2016 | Sedic | |
| 2006/0260619 A1 * | 11/2006 | Moench | A61F 6/08 128/837 |

(Continued)

FOREIGN PATENT DOCUMENTS

| | | |
|---|---|---|
| EP | 0504301 | 3/2004 |
| EP | 2043569 | 3/2010 |

(Continued)

OTHER PUBLICATIONS

Dictionary.com definition of "integral." Accessed Aug. 14, 2019.*

(Continued)

*Primary Examiner* — Tatyana Zalukaeva
*Assistant Examiner* — Jessica R Arble
(74) *Attorney, Agent, or Firm* — Evan Feldstein

(57) ABSTRACT

Menstrual cups and methods of use are described herein. An example menstrual cup may include a rim having at least one lip that extends about the rim and a receptacle defining a textured pattern. The textured pattern may include various lines and/or shapes. An example menstrual cup may be comprised of silicone or a similar material and can be worn during sexual intercourse.

20 Claims, 11 Drawing Sheets

(56) References Cited

U.S. PATENT DOCUMENTS

| | | | |
|---|---|---|---|
| 2007/0289598 A1* | 12/2007 | LaBarre | A61F 6/08 |
| | | | 128/837 |
| 2008/0077097 A1 | 3/2008 | Chambers et al. | |
| 2009/0320855 A1 | 12/2009 | Shihata | |
| 2010/0312204 A1* | 12/2010 | Sheu | A61F 6/08 |
| | | | 604/330 |
| 2013/0267769 A1 | 10/2013 | La Vean | |
| 2015/0164680 A1 | 6/2015 | Chen | |
| 2016/0278988 A1 | 9/2016 | Knox | |
| 2018/0140458 A1* | 5/2018 | Brockway | A61F 5/4553 |
| 2019/0083296 A1* | 3/2019 | Miller | A61F 5/4553 |
| 2019/0358077 A1* | 11/2019 | Bauer | A61F 5/4553 |

FOREIGN PATENT DOCUMENTS

| | | |
|---|---|---|
| FR | 3039060 | 1/2017 |
| WO | WO2007082341 | 7/2007 |

OTHER PUBLICATIONS

Intimina, Intimina.com, "Lily Cups," pp. 1-4, accessed Dec. 10, 2018.

Flexfits, "Flex Starter Kit," flexfits.com, accessed Mar. 5, 2019, pp. 1-7.

* cited by examiner

MENSTRUAL CUPS AND METHODS OF USE

CROSS-REFERENCE TO RELATED APPLICATIONS

This application is a continuation of Non-provisional U.S. patent application Ser. No. 16/214,452, filed Dec. 10, 2018, which claims the benefit of U.S. Provisional Application No. 62/609,513, filed Dec. 22, 2017. This related application is incorporated by reference into this disclosure in its entirety.

FIELD

This disclosure relates to the technical field of feminine hygiene products and methods of use. More specifically, feminine hygiene products configured to collect menstrual fluids and methods of using the same are described herein.

BACKGROUND

Devices configured to absorb menstrual discharge traditionally include menstrual pads and tampons, for example. However, users of such devices are often unsatisfied with such products. Menstrual pads tend to be bulky, uncomfortable, and prone to leakage. Moreover, they cannot be comfortably worn with certain types of clothing. Tampons, which are configured to absorb fluids while disposed within the body, can alter the ratio of various fluids, chemicals, and/or bacteria within the user's body, occasionally leading to toxic shock syndrome and other maladies. Tampons can sometimes scratch and/or irritate the user, as well.

Accordingly, women are increasingly turning to menstrual cups in order to collect and dispose of menstrual fluids and/or discharge and avoid the aforementioned deficiencies with menstrual pads and tampons. Known menstrual cups provide disadvantages of their own, however. Known menstrual cups, for example, are not designed to be worn during sexual intercourse and may generate discomfort if used during intercourse, necessitating removal prior to engaging in the same. Additionally, known menstrual cups occasionally rip, break, or tear when used. Such rips, breaks, or tears typically occur during insertion or removal of a menstrual cup in the portion of the cup configured to collect menstrual fluids. This can be messy and inconvenient.

What is needed, therefore, are improved menstrual cups that can be used during sexual intercourse and are structured to prevent breakages.

BRIEF SUMMARY OF SELECTED EXAMPLES

Various example menstrual cups and methods of use are described and illustrated.

An example menstrual cup comprises a rim having an upper portion, a lower portion, and an exterior surface, the rim defining a first lip adjacent the upper portion, the first lip extending along the exterior surface of the rim, the rim comprising silicone, and a receptacle disposed adjacent and attached to the lower portion of the rim, the receptacle defining an interior surface, the interior surface comprising a textured pattern, the receptacle comprising silicone.

Another example menstrual cup comprises a rim having an upper portion, a lower portion, and an exterior surface, the rim defining a first lip adjacent the upper portion and a second lip adjacent the lower portion, each of the first lip and the second lip extending along the exterior surface of the rim, the rim comprising silicone, and a receptacle disposed adjacent and attached to the lower portion of the rim, the receptacle defining an interior surface, the interior surface comprising a textured pattern comprising lines running in at least three directions along the receptacle, the receptacle comprising silicone, wherein said menstrual cup may be used during sexual intercourse.

Another example menstrual cup comprises a rim having an upper portion, a lower portion, and an exterior surface, the rim defining a first lip adjacent the upper portion and a second lip adjacent the lower portion, each of the first lip and the second lip extending along the exterior surface of the rim and being substantially circular in cross-sectional shape, the rim defining a groove between the first lip and the second lip, the rim comprising silicone, and a receptacle disposed adjacent and attached to the lower portion of the rim, the receptacle defining an interior surface, the interior surface comprising a textured pattern comprising lines running in at least three directions along the receptacle, the lines forming a plurality of shapes with portions of the lines forming edges of the shapes, the plurality of shapes including a plurality of hexagons, the receptacle comprising silicone, wherein said menstrual cup may be used during sexual intercourse, and wherein the first lip and the second lip have the same cross-sectional shape.

Additional understanding of claimed devices and methods may be obtained by reviewing the detailed description of selected examples, below, with reference to the appended drawings.

Figure 1:
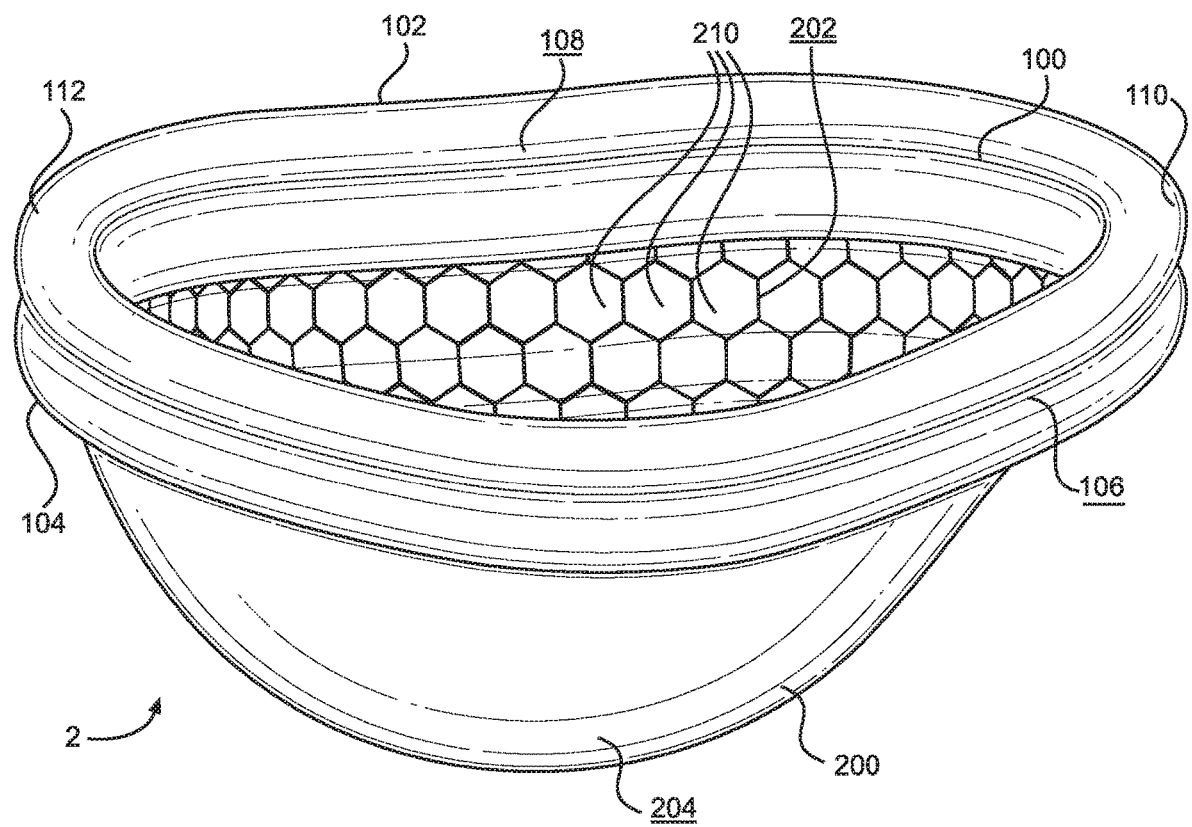
FIG. 1 is a perspective view of an example menstrual cup.

The figures depict various embodiments of the present invention for purposes of illustration only. One skilled in the art will readily recognize from the following discussion that alternative embodiments of the structures and methods illustrated herein may be employed without departing from the principles of the invention described herein.

DETAILED DESCRIPTION OF SELECTED EXAMPLES

The following detailed description and the appended drawings describe and illustrate various menstrual cups and methods of use. The description and drawings are provided to enable one skilled in the art to make and use one or more example menstrual cups and methods of use. They are not intended to limit the scope of the claims in any manner.

Each of FIGS. 1, 2, 3, 4, 5, 6, 7, 8, and 9 illustrates an example menstrual cup 2 or a portion thereof. The menstrual cup 2 includes a rim 100 and a receptacle 200 attached to the rim 100.

In the illustrated embodiment, the rim 100 includes an upper portion 102, a lower portion 104 opposite the upper portion 102 and adjacent the receptacle 200, an exterior surface 106, and an interior surface 108. The rim 100 also includes a first end 110, a second end 112 opposite the first end 110, a first side 114, a second side 116 substantially opposite the first side 114, and a connecting portion 118 that is adjacent the lower portion 104 and extends away from the upper portion 102.

Figure 6:
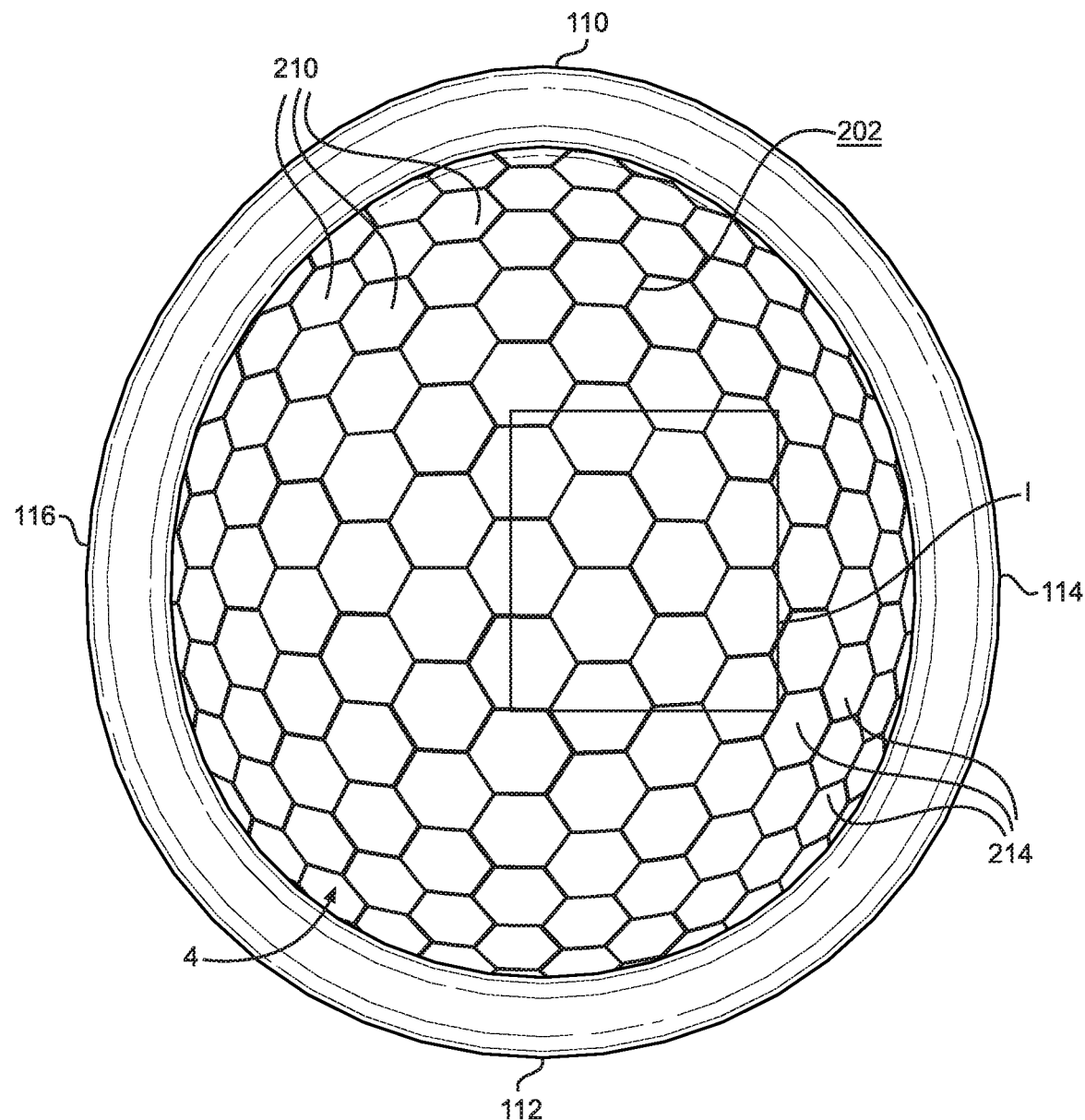
FIG. 6 is a top view of the menstrual cup illustrated in FIG. 1.

The rim 100 is flexible and may be manipulated by the hands of a user such that the shape of the rim 100 may change based on such manipulation. When not in use, the rim 100 is substantially oval in shape when viewed from above, as is illustrated in FIG. 6. The rim may be comprised of various elastic materials, including materials that are soft and do not damage the skin, such as silicone, in various embodiments. Silicone is used as an example throughout, though it is understood that other similar materials can be used, as well. Additionally, the rim may have any suitable shape in different embodiments. A skilled artisan will be able to select a suitable shape and suitable materials for the rim according to a particular example based on various considerations, including the desired size and shape of the receptacle and the projected dimensions of the bodies of the users for which the device is designed. In various embodiments, the rim may be comprised of one or more polymers, silicone compounds, plastics, TPE, TPEE, PTE, high-density foams, various other soft materials, and/or any combination thereof. In different embodiments, the rim may be circular, elliptical, egg-shaped, triangular, rectangular, ovoid, hexagonal, and any other suitable shape.

Figure 8:
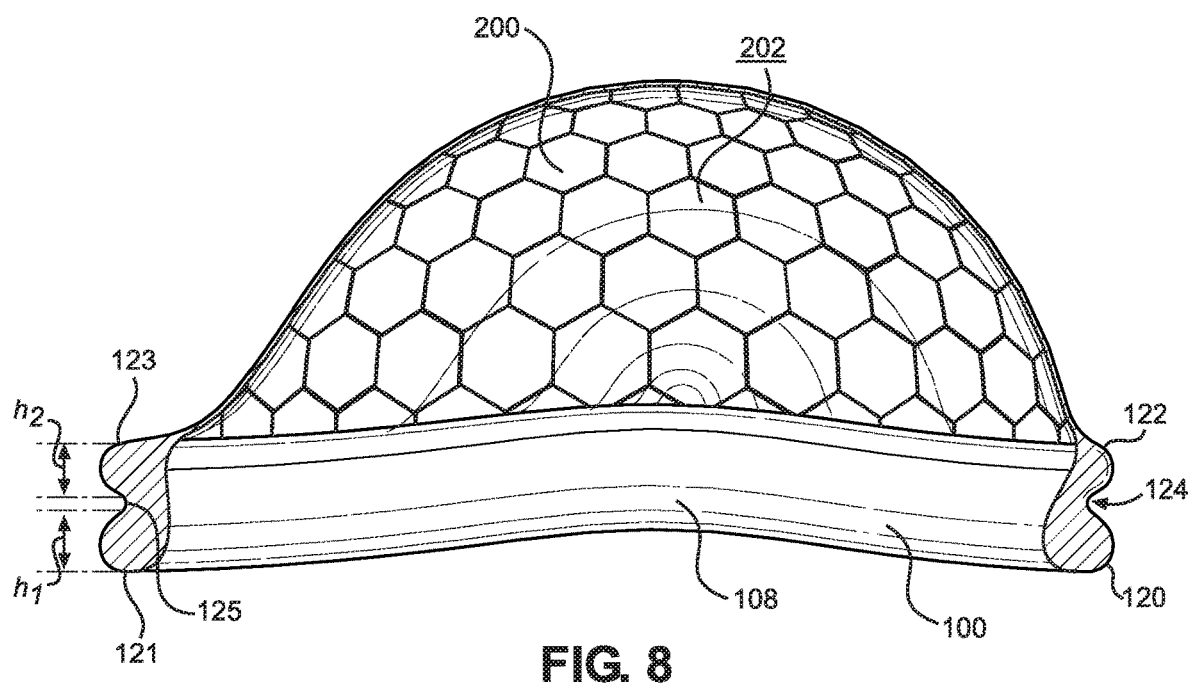
FIG. 8 is a cross-sectional view of the menstrual cup illustrated in FIG. 1, taken along line 8-8 in FIG. 5.

The exterior surface 106 of the rim 100 is configured such that it may be contacted by a user prior to and during insertion of the menstrual cup 2. The exterior surface 106 defines a first lip 120, a second lip 122, and a groove 124 disposed between and defined by the first lip 120 and the second lip 122. The first lip 120 is substantially adjacent the upper portion 102 and the second lip 122 is substantially adjacent the lower portion 104. The first lip 120 and the second lip 122 extend along the entire length of the rim 100. Specifically, each of the first and second lips 120, 122 extends about the exterior surface 106 of the rim 100. Consequently, the groove 124 also extends along the entire length of the rim 100. In the illustrated embodiment, each of the first and second lips 120, 122 are substantially semicircular in cross-sectional shape (as best illustrated in FIG. 8). However, in other embodiments, the first and second lips may have any suitable shape. A skilled artisan will be able to select suitable lips and grooves according to a particular example based on various considerations, including the shape and size of the rim and the shape and size of the receptacle. In various embodiments, the rim may have zero, one, three, or more than three lips. In different embodiments, one or both of the lips may have any cross-sectional shape, including circular, triangular, rectangular, square, elliptical, semi-elliptical, ovoid, semi-ovoid, and/or any other suitable shape. In some embodiments, one lip differs in shape from the other lip. Additionally, in an example embodiment the first lip and second lip may be symmetrical to one another about a plane extending through the center of the groove; the lips may be asymmetrical in different embodiments. In other embodiments, one or more of the first lip, the second lip, and the groove may only extend along a portion of the exterior surface of the rim.

The first lip 120 has a first height $h_1$ and the second lip 122 has a second height $h_2$ in the illustrated embodiment. The first height $h_1$ extends from a plane (not illustrated in the Figures) extending along the top 121 of the first lip 120 to a plane (not illustrated in the Figures) extending along the base 125 of the groove 124. The second height $h_2$ extends from a plane (not illustrated in the Figures) extending along the bottom 123 of the second lip 122 to the plane extending along the base 125 of the groove 124. In the illustrated embodiment, the first height $h_1$ is equal to the second height $h_2$. However, in other embodiments, any suitable first and second heights may be used. A skilled artisan will be able to determine suitable first and second heights according to a particular example based on various considerations, including the shape and size of the rim and the shape and size of the receptacle. In some embodiments, the first height is larger than the second height. In other embodiments, the second height is larger than the first height. In various embodiments, the first height may be between about 0.1 millimeters ("mm") and about 10 mm, between about 0.5 mm and about 5 mm, and between about 1 mm and about 2 mm. In various embodiments, the second height may be between about 0.1 mm and about 10 mm, between about 0.5 mm and about 5 mm, and between about 1 mm and about 2 mm. In alternative embodiments, the first and/or second height may be calculated differently; for example, height may not extend to the top and/or bottom of a lip and it may not fully extend to the base of the groove in such embodiments.

The interior surface 108 of the rim 100 does not define one or more lips. However, in other embodiments, the interior surface may define lips and/or grooves.

The rim 100 also includes a connecting portion 118 extending from the lower portion 104 away from the upper portion 102. The connecting portion 118 directly contacts the receptacle 200 of the menstrual cup 2. In fact, the receptacle 200 is integrally formed with the connecting portion 118 (and, thus, the rim 100). The connecting portion 118 extends along the lower portion 104.

Figure 2:
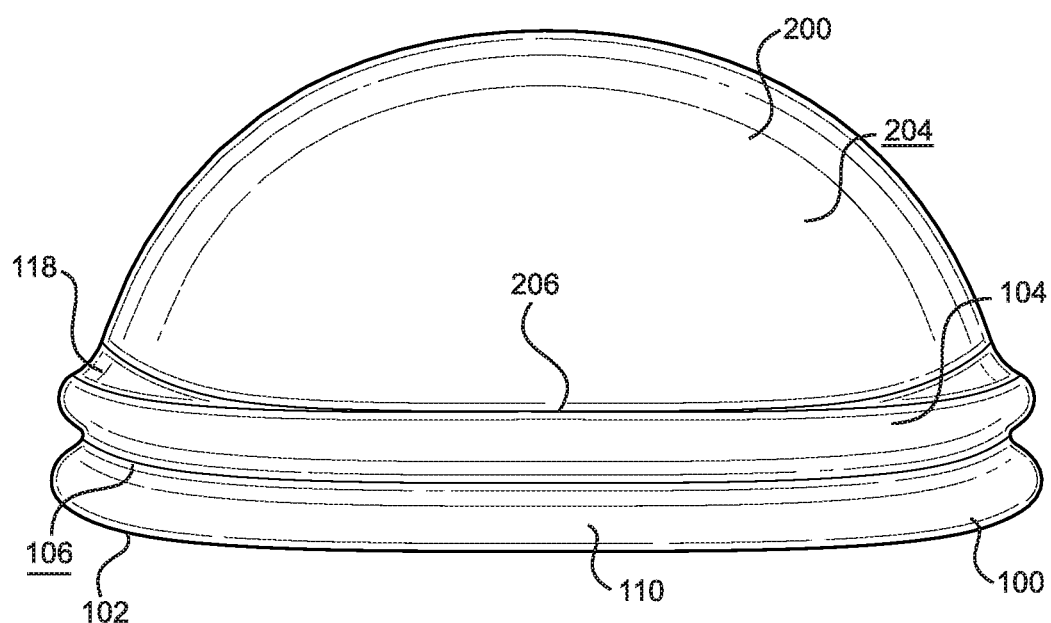
FIG. 2 is an end view of the menstrual cup illustrated in FIG. 1.
Figure 3:
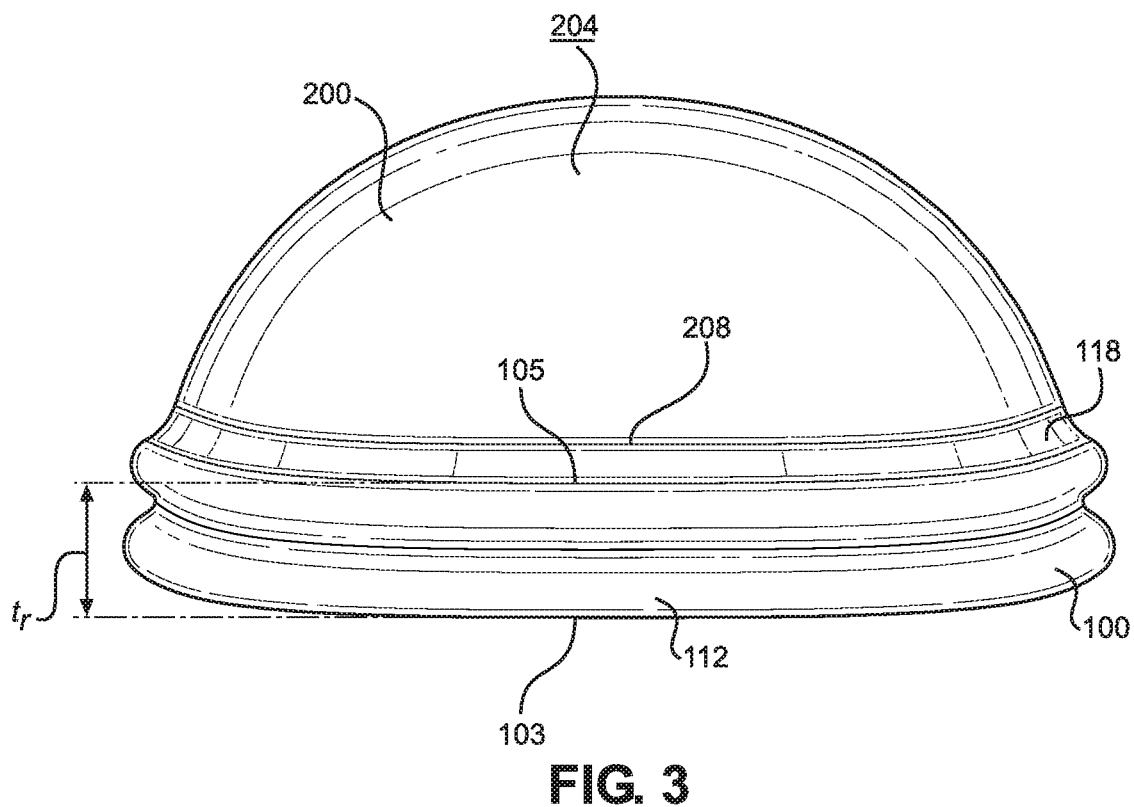
FIG. 3 is another end view of the menstrual cup illustrated in FIG. 1.
Figure 4:
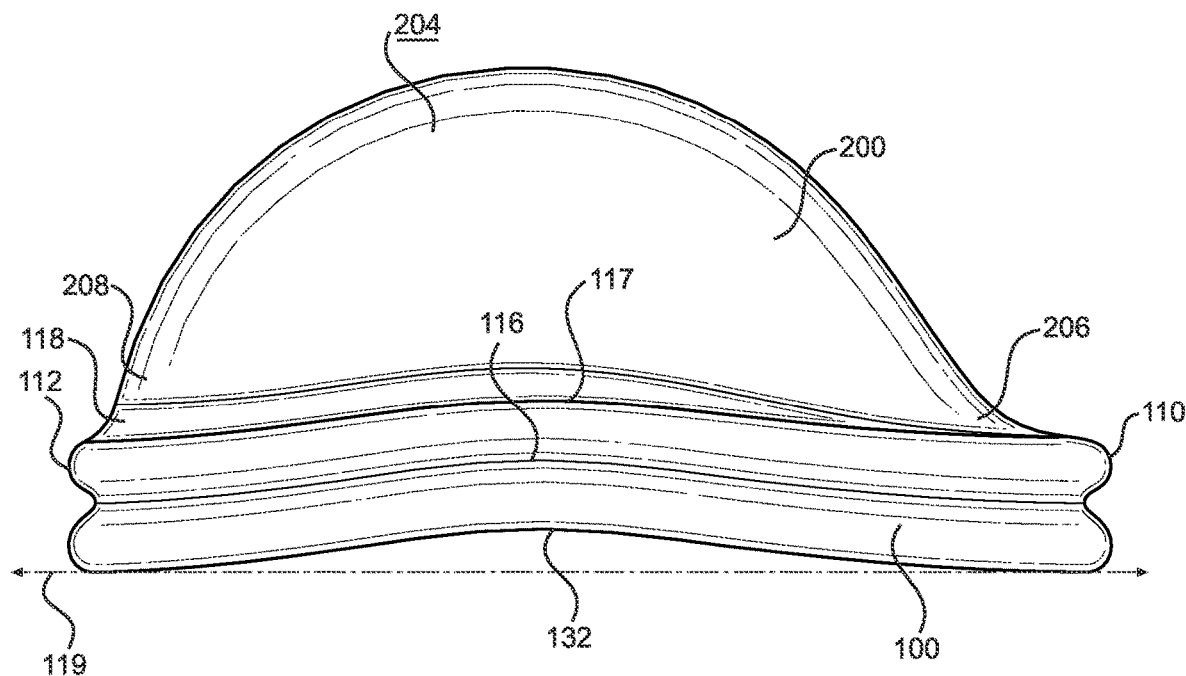
FIG. 4 is a side view of the menstrual cup illustrated in FIG. 1.
Figure 5:
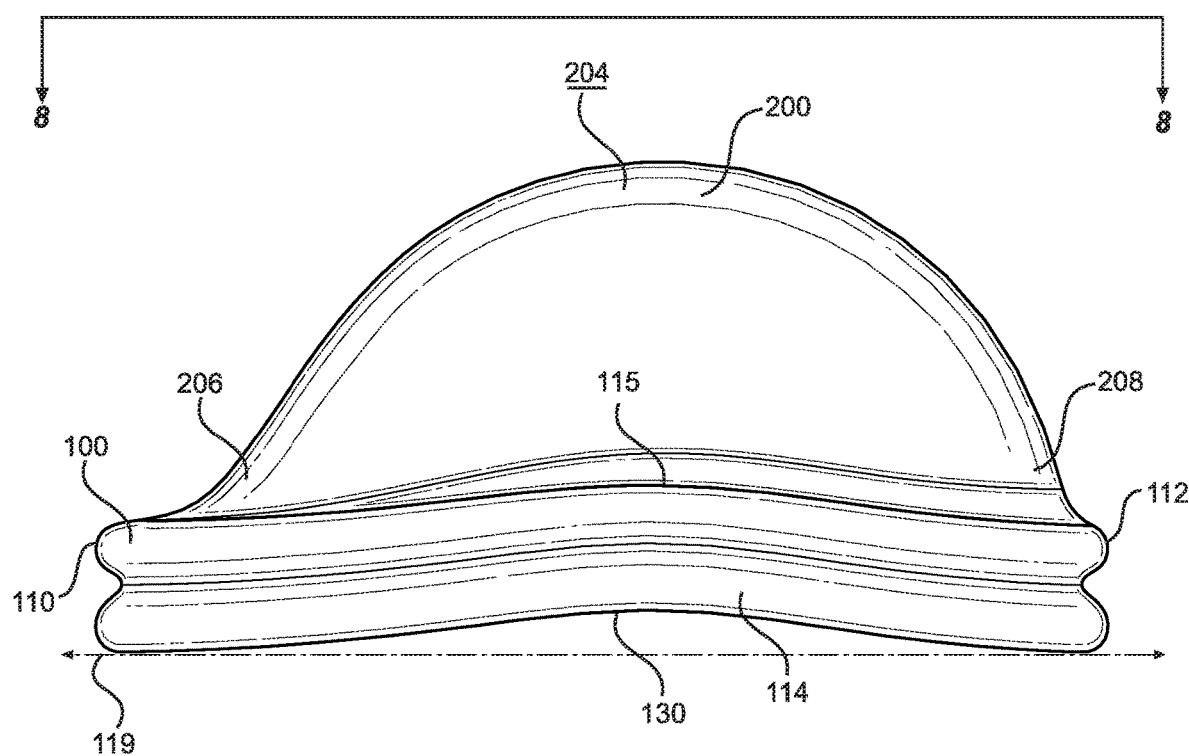
FIG. 5 is another side view of the menstrual cup illustrated in FIG. 1.
Figure 7:
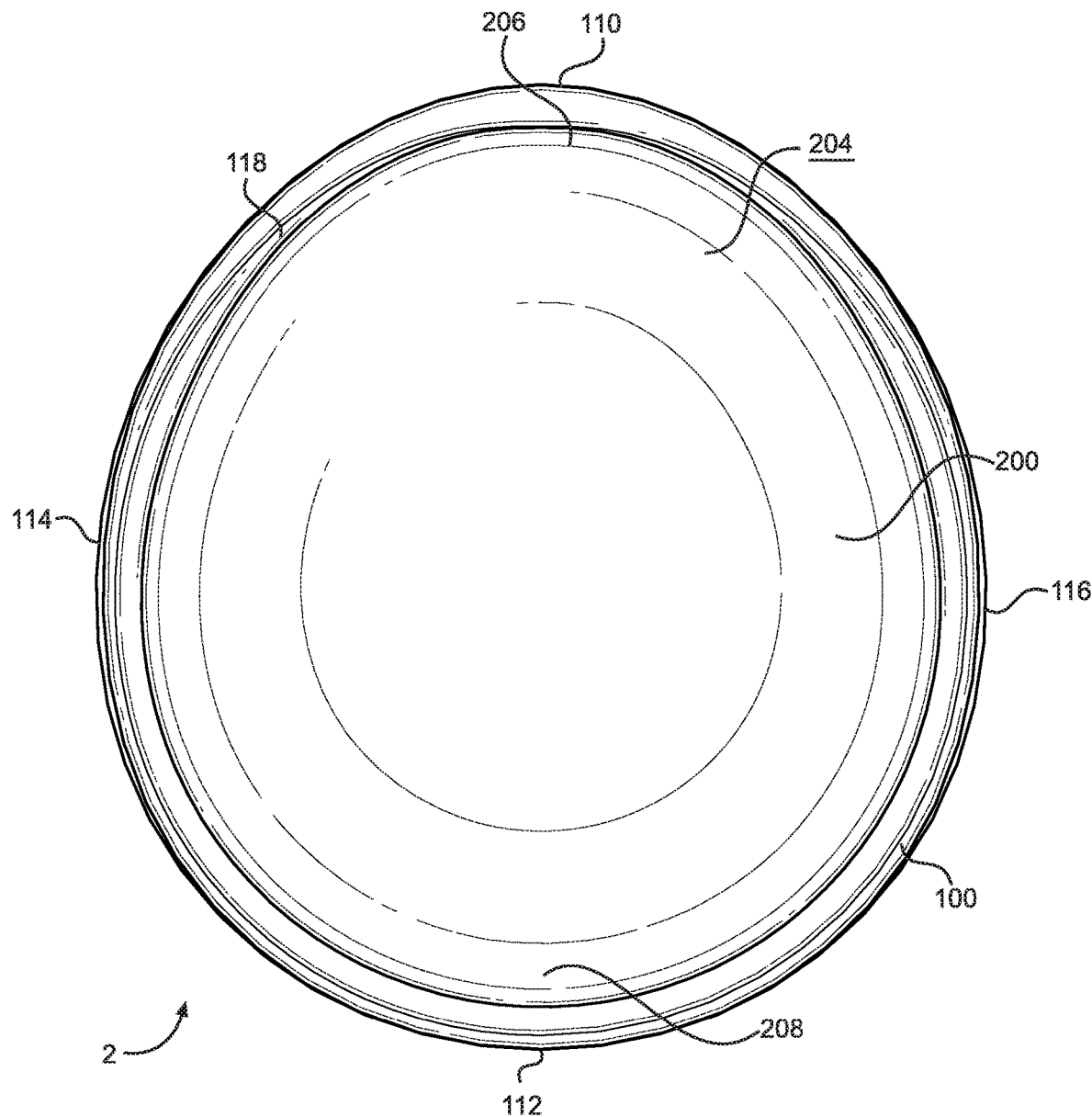
FIG. 7 is a bottom view of the menstrual cup illustrated in FIG. 1

The connecting portion 118, however, is not uniform in thickness along its entire length (thickness being measured by the distance to which the connecting portion 118 extends away from the lower portion 104). Indeed, as is illustrated in FIGS. 2 and 7, the connecting portion 118 thins as it approaches the first end 110 of the rim 100 as compared to its thickness adjacent the second end 112. FIGS. 3, 4, 5, and 7 illustrate the connecting portion 118 having a thickness that is substantially uniform at and about the second end 112 (FIG. 3) as it extends toward the first side 116 (FIG. 4) and the second side (FIG. 5). FIG. 7 shows the connecting portion 118 with relation to the rest of the rim 100 in its entirety. However, as noted above, as the connecting portion 118 approaches the first end 110, it noticeably decreases in thickness. A skilled artisan will be able to determine how to suitably configure the connecting portion according to a particular example based on various considerations, including the size and shape of the first and second lips and the manner in which the connecting portion shall contact and/or attach to the receptacle. In some embodiments, the receptacle may be attached to the connecting portion via a mechanical attachment or an adhesive, rather than being integrally formed with the same. In other embodiments, the connecting portion may have a constant thickness along its entirety. In different embodiments, the connecting portion may be adjacent one or more of the first end, second end, first side, and/or second side and may not extend completely around the rim. In an alternative embodiment, the connecting portion may comprise the second lip.

The rim 100 is also curved at various portions. More specifically, as is illustrated in FIGS. 4 and 5, the second side 116 and the first side 114 extend toward the receptacle 200 at both the upper portion 102 and lower portion 104 of the rim 100 and away from a plane 119 containing a portion of the first end 110 and the second end 112. This occurs adjacent the approximate midpoint 115 of the first side 114 and the approximate midpoint 117 of the second side 116. Accordingly, the first side 114 defines a first curved portion 130 and the second side 116 defines a second curved portion 132. When the menstrual cup 2 is placed on a flat surface, such as a table, neither of the first or second curved portions 130, 132 will contact the flat surface; instead, the first end 110 and the second end 112 of the rim 100 will do so. The first and second curved portions 130, 132 may be angled relative to the first and second ends or any other portion of the menstrual cup to any degree in various embodiments. Therefore, in various embodiments, the particular angle and/or curve of one or both of the curved portions may be sharp, rolling, slight, and comprise any angle to any degree. A skilled artisan will be able to determine how to suitably configure the first and second sides and curved portions relative to the first and second ends and/or other portions of the menstrual cup according to a particular example based on various considerations, including the shape and size of the receptacle and the user for which the device is designed. In some embodiments, the entire upper and lower portions of the rim may be flat, such that the sides are on substantially the same planes as the first and second ends. In another embodiment, only one of the sides may be curved. In a different embodiment, the menstrual cup may be configured such that the sides would contact a flat surface when placed thereupon, but one or both of the first and second ends may not.

The rim 100 also defines a rim thickness $t_r$. The rim thickness $t_r$ extends from the top 103 of the upper portion 102 to the base 105 of the lower portion 104 but does not include the connecting portion 118. The rim thickness $t_r$ is illustrated in FIG. 3. In the illustrated embodiment, the rim thickness $t_r$ is constant about the entire rim 100; however, in other embodiments, the rim thickness may differ along the length of the rim. A skilled artisan will be able to determine a suitable rim thickness according to a particular example based on various considerations, including the shapes and sizes of the receptacle and connecting portion. In various embodiments, the rim thickness may be between about 0.1 mm and about 20 mm, between about 1 mm and about 10 mm, and between about 4 mm and about 8 mm.

The receptacle 200 is integrally formed with the connecting portion 118 such that it is substantially adjacent the lower portion 104. The receptacle 200 is configured to collect fluid, such as menstrual fluid; it is shaped accordingly. The receptacle 200 includes an interior surface 202, an exterior surface 204, a first end 206 substantially adjacent the first end 110 of the rim 100, and a second end 208 opposite the first end 206 and substantially adjacent the second end 112 of the rim 100. In the illustrated embodiment, the receptacle 200 is comprised of silicone. In other embodiments, however, the receptacle may be comprised of one or more polymers, silicone compounds, plastics, TPE, TPEE, PTE, high-density foams, various other soft materials, and/or any combination thereof.

The receptacle 200 is designed to collect menstrual fluid while it is worn by a user. More specifically, the receptacle 200 collects menstrual fluid within a cavity 4 cooperatively defined by the receptacle 200 and the rim 100. The receptacle 200, therefore, includes a textured pattern 210 configured to aid in resisting ripping, tearing, and/or breaking of the receptacle 200 of the menstrual cup 2. The textured pattern 210 is integrally formed with the receptacle 200.

The textured pattern can cover any portion of the receptacle in some embodiments; the illustrated embodiments provide only some examples of the same. In the illustrated embodiment, the textured pattern 210 covers only the interior surface 202. In other embodiments, it may also cover the exterior surface. The textured pattern may extend all the way to the connecting portion (or the lower portion), or it may cease prior to being disposed adjacent the connecting portion (and/or lower portion) in various embodiments. A skilled artisan will be able to determine how to suitably configure the textured portion according to a particular example based on various considerations, including the size and shape of the receptacle and the desired strength of the same. In some embodiments, the textured pattern may cover between about 10% and about 100% of the interior surface, between about 25% and about 75% of the interior surface, between about 40% and about 60% of the interior surface, and any values or fractional values in between these ranges. In another embodiment, the textured pattern may not be continuous but can appear in disconnected portions along the receptacle, such as in strips along the interior surface. The textured pattern can further be focused on one portion of the receptacle. The textured pattern may also appear in particular areas anywhere along the receptacle, such as in circular or square patches that may or may not be connected. These are merely examples of how the textured pattern can be arranged; other designs are also possible.

In various embodiments, the textured pattern may be created in the receptacle in a number of manners. In one example, the textured pattern can include ridges or indentations that are molded to in an interior or exterior surface of the receptacle. The textured pattern could also be made up of fibers or a mesh that is embedded within layers of the receptacle or is placed on an exterior or interior surface in other embodiments. In yet other embodiments, the textured pattern may be placed atop the interior surface of the receptacle and held in place via any suitable mechanism, including via one or more mechanical attachments and/or an adhesive.

Textured patterns may serve a number of functions and may include a number of designs. For example, in one embodiment the textured pattern may comprise fibers or a mesh integrally formed with the receptacle, increasing the tensile strength of the receptacle as compared to receptacles not having this textured pattern. This aids in reducing the likelihood of breaking or tearing. In some embodiments, the lines are formed as fibers or a reinforcing mesh wrapping on or about the receptacle. Alternatively, the textured pattern may increase the elasticity of the receptacle, decreasing the likelihood that the menstrual cup will be lodged in an uncomfortable position when worn, which could necessitate removing the device. In additional embodiments, the textured pattern can assist in preventing menstrual fluids from exiting the menstrual cup by providing structures which prevent fluid from easily exiting the cavity. Such fluids may be trapped within the textured patterns (i.e., trapped by the shapes themselves). Textured surface which are molded to the interior surface of the receptacle could function thusly in some embodiments.

Figure 9:
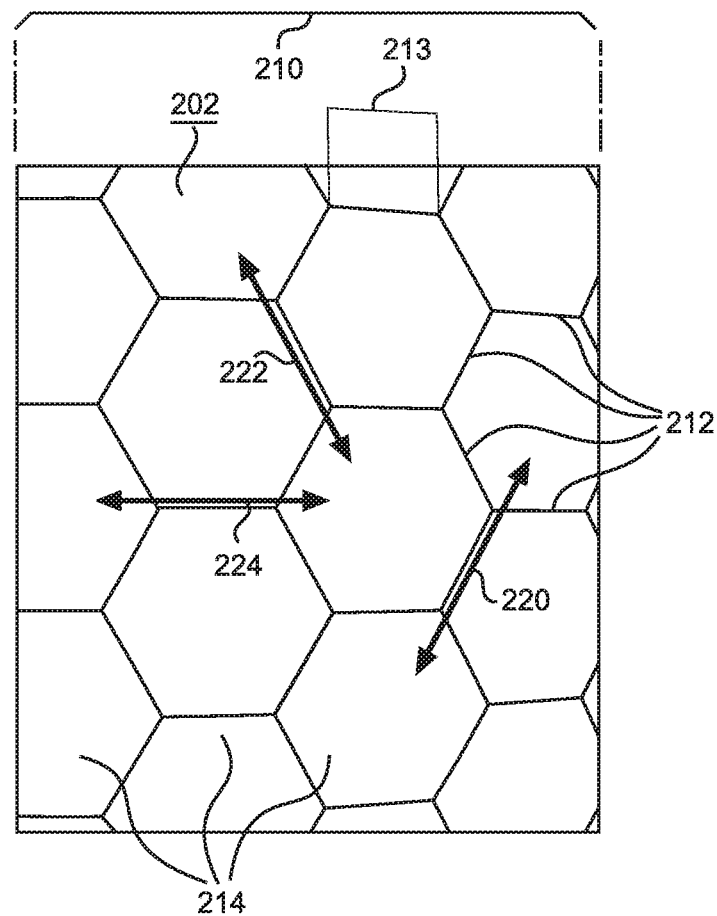
FIG. 9 is a magnified end view of Area I of the menstrual cup illustrated in FIG. 6.

FIG. 9 is a magnified view of the textured pattern 210, as described in the present embodiment. The textured pattern 210 includes lines 212 running along the receptacle 200. The lines 212 run in three directions, including two diagonal directions and one horizontal direction. The lines form shapes 214 in the textured pattern 210; the shapes 214 are generally hexagonal in this embodiment (aside from those shapes that are adjacent the connecting portion 118) and, accordingly, have six sides. Portions of the lines 212 form edges of the shapes 214. In fact, two shapes can share a single line 212, as illustrated in FIG. 9 which shows a single line 213 shared by two hexagons. The textured pattern 210 is a honeycomb lattice that is formed by the hexagons comprising the shapes 214 (also sometimes known as a chicken-wire design). As illustrated in FIGS. 1 and 6, the shapes 214 comprising the honeycomb lattice are irregularly sized or stretched in certain areas, such as areas near the connecting portion 118. Additionally, some of the shapes 214 near the connecting portion 118 and/or lower portion 104 may include incomplete hexagons. In other embodiments, the lines can run in directions or along axes on the receptacle which differ from those illustrated and described herein. In other embodiments, the lines may form any shape, as is further described below.

FIG. 9 illustrates directional lines 220, 222, 224 along with the lines 212 and shapes 214, as well. The directional lines 220, 222, 224 are shown to run in, respectively a first, a second, and a third direction. As noted above, each line 212 forms a portion of at least two shapes 214 of the textured pattern 210. More specifically, each individual line of the lines 212 forms only one side of two of the hexagons. Thus, generally, the hexagons in the illustrated embodiment share six edges with other hexagons in the textured pattern 210. None of the edges of the shapes 214 are formed by a continuous line 212 running in a single direction (as illustrated by the directional lines 220, 222, 224) across more than one shape 214.

A skilled artisan will be able to select suitable lines and shapes according to a particular example based on various considerations, including the size and shape of the receptacle and the desired strength of the same. In different embodiments, one or more of the lines may be straight or curved along all or any portion, may be grouped together or separate, may intersect or not, may have different thicknesses, widths, lengths, or heights. In such embodiments, the width, length, and height may vary across a single menstrual cup, among other design variations. Any of the patterns can be turned in any direction such that the lines run at different angles relative to the receptacle than is shown, as well. Any line angle relative to a vertical or horizontal axis of the menstrual cup is possible (e.g., 5, 10, 20, 30, 40, 50, 60, 70, 80, 90, 100, 130, 150, 170-degree angles or fractional values in between or any ranges including any of these numbers). In various embodiments, the shapes may include one or more circles, triangles, pentagons, squares, rectangles, heptagons, ovals, ellipses, and any other suitable shapes. In other embodiments, one or more of the lines may include solid lines, broken lines, dots, or other structures formed as a line, or other designs for providing a structure that can form the edge of a shape. In different embodiments, the shapes can be irregular or have unequal sides; additionally, a single textured pattern may include multiple shapes, such as hexagons, triangles, and diamonds, for example. The shapes can be composed of shapes that include at least 3, 4, 5, 6, 7, 8, 9, or 10 sides in various examples, as well.

Figure 10:
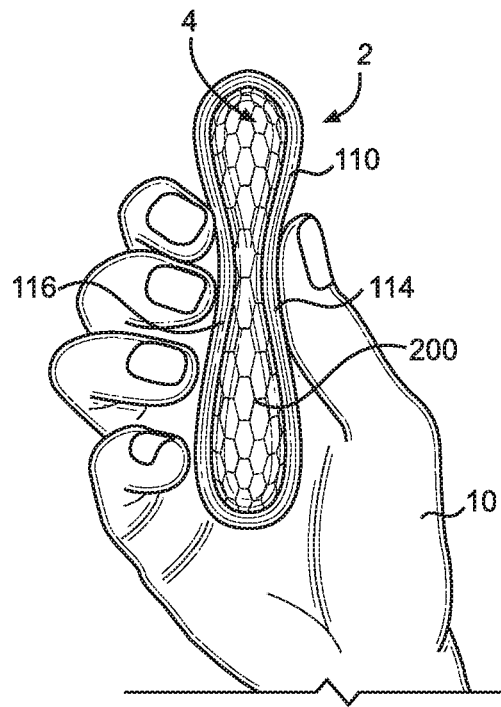
FIG. 10 is a perspective view of the menstrual cup illustrated in FIG. 1 in the hand of a user.

In use, the menstrual cup 2 is first grasped by the hand 10 of a user, as illustrated in FIG. 10. More specifically, the user grasps the menstrual cup 10 by the rim 100 and compresses the device via compressive force generated by the hand 10. This causes the menstrual cup 2 to deform in shape, with the first side 114 of the rim 100 being disposed closer to the second side 116 of the rim 100 as compared to when the menstrual cup 2 is not compressed by a user. Grasping the menstrual cup 2 in this manner readies the device for insertion within the body.

Figure 11:
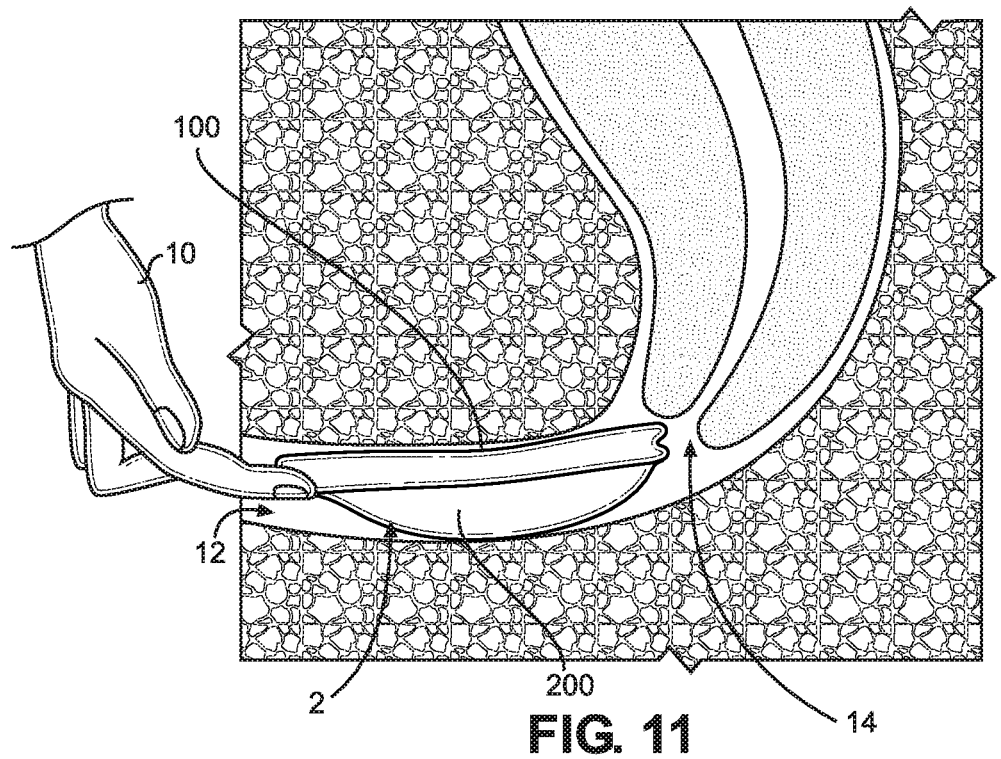
FIG. 11 is a sectional view of a portion of the body of the user during placement of the menstrual cup illustrated in FIG. 10 within the body of the user.

After a user has compressed the menstrual cup 2, the user then inserts the device through the vaginal canal 12 and adjacent and/or beneath the cervix 14. This is illustrated in FIG. 11. The user is able to adjust the particular position of the menstrual cup 2 within the body at this point, if necessary, through use of the fingers of the hand 10.

Figure 12:
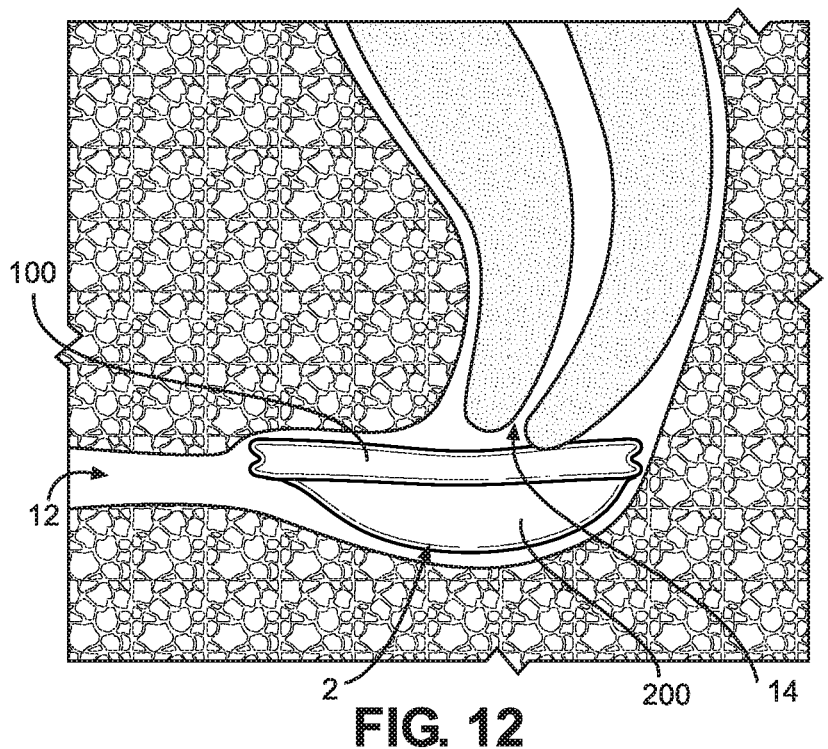
FIG. 12 is a side view of a portion of the body of the user and the menstrual cup illustrated in FIG. 11 after the menstrual cup has been placed within the body of the user.

FIG. 12 illustrates the menstrual cup 2 once it has been positioned within a user and is ready to be used. As noted previously, the menstrual cup 2 is situated within the body such that a wearer of the device may have sexual intercourse with little to no discomfort due to the presence of the menstrual cup 2.

Figure 13:
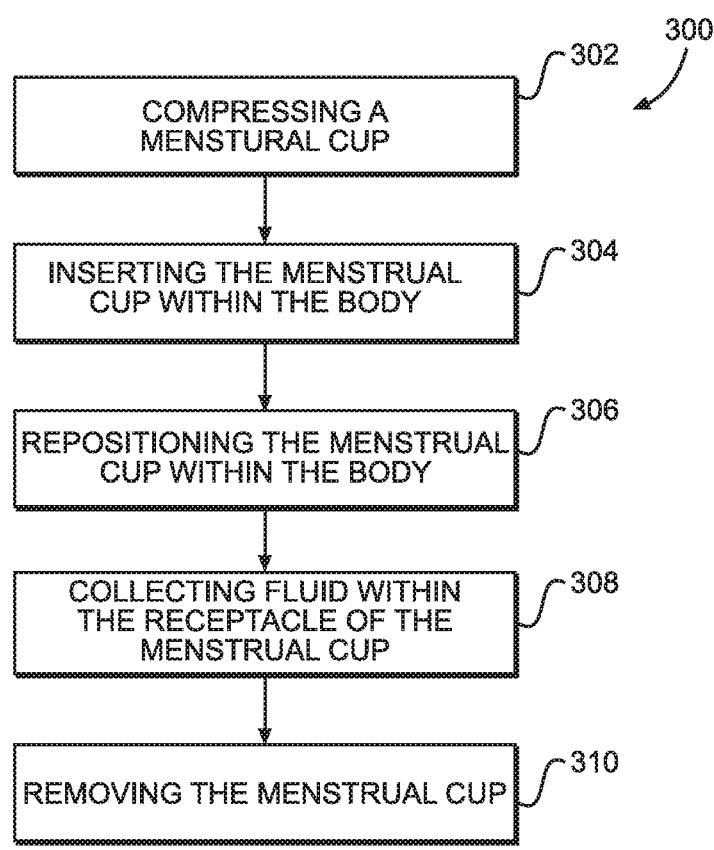
FIG. 13 is a flowchart representation of an example method of using a menstrual cup.

FIG. 13 is a flowchart representation of an example method 300 of using a menstrual cup. Performance of this method results in the placement of a menstrual cup within the body. Any menstrual cup can be used with this method.

An initial step 302 comprises a user compressing a menstrual cup, such as menstrual cup 2, with her hand such that a first side and a second side of a rim, such as first side 114 and second side 116 of rim 100, are disposed closer to one another than were the first and second sides 114, 116 in a non-compressed state.

Another step 304 comprises a user inserting the menstrual cup 2 within her body, within and/or through her vaginal canal, and beneath and/or adjacent her cervix.

Optionally, another step 306 comprises re-positioning the menstrual cup 2 within the body such that it is satisfactorily placed.

Another step 308 comprises collecting menstrual fluid and/or discharge within the receptacle 200 of the menstrual cup 2.

Another step 310 comprises removing the menstrual cup 2 from the body of the user.

It is noted that the method 300 may be completed in the order illustrated and described. However, the steps may be completed in any order.

In all examples, a menstrual cup and its various components may be formed of any suitable material, including presently known and later-developed materials. A skilled artisan will be able to determine appropriate materials for menstrual cups based on various considerations, including the size and shape of the menstrual cups.

Those with ordinary skill in the art will appreciate that various modifications and alternatives for the described and illustrated embodiments can be developed in light of the overall teachings of the disclosure. Accordingly, the particular arrangements disclosed are intended to be illustrative only and not limiting as to the scope of the invention, which is to be given the full breadth of the appended claims and any and all equivalents thereof.

What is claimed is:

1. A menstrual cup, comprising:
   a rim having an upper portion, a lower portion, an exterior surface, a first end, a second end, a first side, and a second side, the rim defining a first lip adjacent the upper portion, the first lip extending along the exterior surface of the rim, the rim comprising silicone and having a substantially regular oval shape; and a receptacle disposed adjacent and attached to the rim, the receptacle comprising silicone and defining an interior surface, the interior surface comprising a textured pattern defined solely by the interior surface, wherein a slope of a first end of the receptacle adjacent to the first end of the rim is less than a slope of a second end of the receptacle adjacent to the second end of the rim;

wherein the rim is integrally formed with the receptacle; and wherein the first end of the rim extends away from the receptacle.

2. The menstrual cup of claim 1, further comprising a second lip adjacent the lower portion, the second lip extending along the exterior surface of the rim.

3. The menstrual cup of claim 2, wherein the rim defines a groove disposed between the first lip and the second lip.

4. The menstrual cup of claim 3, wherein the first lip extends about the entire exterior surface of the rim.

5. The menstrual cup of claim 4, wherein the second lip extends about the entire exterior surface of the rim.

6. The menstrual cup of claim 5, wherein each of the first lip and the second lip is substantially semi-circular in cross-sectional shape.

7. The menstrual cup of claim 6, wherein the first lip defines a first height and the second lip defines a second height; and wherein the first height is substantially equal to the second height.

8. The menstrual cup of claim 7, wherein the rim defines an interior surface that does not define a lip.

9. The menstrual cup of claim 3, wherein the first side of the rim defines a first curved portion.

10. The menstrual cup of claim 9, wherein the second side of the rim defines a second curved portion.

11. The menstrual cup of claim 10, wherein the first end and the second end of the rim are configured to contact a flat surface when the rim is placed on said flat surface.

12. The menstrual cup of claim 11, wherein neither the first curved portion nor the second curved portion is configured to contact said flat surface when the rim is placed on said flat surface.

13. The menstrual cup of claim 3, wherein the rim defines a thickness extending from a top of the upper portion to a base of the lower portion; and wherein the rim thickness is substantially uniform about the entirety of the rim.

14. The menstrual cup of claim 13, wherein the rim further comprises a connecting portion that is integrally formed with the receptacle.

15. The menstrual cup of claim 14, wherein the connecting portion defines a thickness; and wherein the thickness is greater adjacent the second end than the first end.

16. The menstrual cup of claim 1, wherein the receptacle extends from the first end to the second end of the rim.

17. A menstrual cup, comprising:

a rim having an upper portion, a lower portion, an exterior surface, a first end, a second end, a first side, a second side, and a curved portion, the rim defining a first lip adjacent the upper portion, the first lip extending along the exterior surface of the rim, the rim comprising silicone and having a substantially regular oval shape, the curved portion disposed adjacent said rim and tapering in side as it extends toward the first end from the second end; and a receptacle disposed adjacent and attached to the rim, the receptacle comprising silicone and defining an interior surface, the interior surface comprising a textured pattern defined solely by the interior surface, wherein a slope of a first end of the receptacle adjacent to the first end of the rim is less than a slope of a second end of the receptacle adjacent to the second end of the rim;

wherein the rim is integrally formed with the receptacle; and wherein the first end of the rim extends away from the receptacle.

18. The menstrual cup of claim 17, wherein the receptacle extends from the first end to the second end of the rim.

19. The menstrual cup of claim 18, further comprising a second lip adjacent the lower portion, the second lip extending along the exterior surface of the rim.

20. The menstrual cup of claim 19, wherein the first lip defines a first height, the second lip defines a second height, and each of the first height and the second height is between 0.1 millimeters and 10 millimeters.

\* \* \* \* \*